United States Patent [19]

Davis et al.

[11] Patent Number: 5,081,151
[45] Date of Patent: Jan. 14, 1992

[54] METHOD OF GROWING HAIR

[75] Inventors: Michael F. A. Davis; Walter T. Gibson, both of Northamptonshire, England

[73] Assignee: Cheesebrough-Pond's USA Co., division of Conopco, Inc., Greenwich, Conn.

[21] Appl. No.: 454,337

[22] Filed: Dec. 21, 1989

[30] Foreign Application Priority Data

Dec. 22, 1988 [GB] United Kingdom ............... 8830019

[51] Int. Cl.$^5$ ............................................. A61K 31/19
[52] U.S. Cl. ................................... 514/574; 514/547; 514/880
[58] Field of Search .................... 514/574, 547, 880

[56] References Cited

U.S. PATENT DOCUMENTS 4,139,619  2/1979  Chidsey ............................ 514/230.8
4,234,599  11/1980 Van Scott et al. ................... 424/279

FOREIGN PATENT DOCUMENTS 0242967  10/1987  European Pat. Off.
0277428  12/1987  European Pat. Off.

OTHER PUBLICATIONS

Chemical Abstracts 111: 120607k (1989).
European Search Report and Annex (EP 89 31 3334).

*Primary Examiner*—Leonard Schenkman
*Attorney, Agent, or Firm*—Milton L. Honig

[57] ABSTRACT

A method for inducing, maintaining or increasing hair growth which is achieved by topically applying a preserved composition to mammalian skin and hair in a mammal having need thereof, the composition comprising a hexosaccharic acid, salts and esters thereof, in an amount sufficient to induce, maintain or increase hair growth.

11 Claims, No Drawings

METHOD OF GROWING HAIR

FIELD OF THE INVENTION

The invention relates to cosmetic and pharmaceutical compositions for topical application to mammalian skin or hair, containing a hair growth promotor which is capable of increasing or maintaining hair growth, especially terminal hair growth on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:

(i) an active stage known as anagen, during which the hair follicle penetrates deep into the dermis with the cells of the bulb dividing rapidly and differentiating to form the hair, (ii) a regressive stage known as catagen, which is heralded by the cessation of mitosis, and during which the follicle regresses upwards through the dermis and hair growth ceases, (iii) a resting stage known as telogen, in which the regressed follicle contains a small secondary germ with an underlying ball of tightly packed dermal papilla cells.

The initiation of a new anagen stage is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is usually a painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, for prolonging anagen and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil.

In addition to the alleged benefits of employing the pyrimidine carbamates of Bazzano or minoxidil of Upjohn, many other hair regrowth studies have been reported in the literature.

Unilever in EP 0 277 428 report that glycosaminoglycan breakdown is an important early change in catagen, and since there is already evidence for a link between the presence of intact glycosaminoglycans and hair growth, they suggest that prevention of proteoglycan and glycosaminoglycan breakdown may lead to earlier onset and/or prolongation of anagen. This would effectively retard hair loss and reverse baldness. Unilever also suggest that such breakdown may be prevented in a number of ways, viz by inhibiting proteoglycanase activity, by blocking cellular uptake of intact glycosaminoglycan chains, and/or by inhibiting glycosaminoglycanase activity. With particular reference to glycosaminoglycanase activity, Unilever have shown that glucaro-1,4-lactone, and related aldonolactones, inhibitors of exoglycosidases, can be topically applied to human skin to induce, maintain or increase hair growth.

We have now identified a new inhibitor of exoglycosidases, which is also believed to prevent the breakdown of glycosaminoglycan chains, and we have accordingly found that this new inhibitor will stimulate hair growth.

DEFINITION OF THE INVENTION

Accordingly, the invention provides a preserved composition suitable for topical application to mammalian skin or hair for inducing, maintaining or increasing hair growth which comprises, as the hair growth promoter, a hexosaccharic acid and/or a salt or ester thereof; the total amount of hexosaccharic acid or salt or ester thereof present in the composition being sufficient to increase hair growth in the rat, when the composition is applied topically thereto over a period of no more than 3 months, by at least 10% more than that obtainable using a control composition from which the promoter has been omitted, in accordance with the Rat Hair Growth Test.

By "preserved composition", we mean that the composition is free from viable microbial contaminants capable of resulting in microbial spoilage of the composition and/or biodegradation of the hair growth promoter.

DISCLOSURE OF THE INVENTION

The Hair Growth Promoter

The composition according to the invention comprises, as a hair growth promoter, an hexosaccharic acid or an acylated hexosaccharic acid, or a salt or ester thereof, having the structure (1).

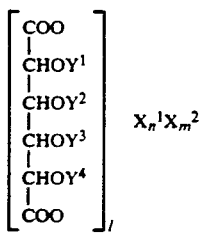

where
- $X^1$ is chosen from H, alkalimetal, ammonium and substituted ammonium counterions;
- $X^2$ is chosen from an alkyl or hydroxyalkyl group having from 1 to 18 carbon atoms;
- $Y^1$, $Y^2$, $Y^3$ and $Y^4$ are each chosen from H, an alkyl group having from 1 to 12 carbon atoms, and an acyl group having from 1 to 18 carbon atoms;
- l is an integer of from 1 to 3;
- m and n are each 0 or the integer 1 or 2; and
- m+n is 1 or 2.

Examples of hexosaccharic acids, in which $X^1$, $Y^1$, $Y^2$, $Y^3$ and $Y^4$ in the above structure are —H, n is 2, and m is 0, include:

Allosaccharic acid
Altrosaccharic acid
Glucosaccharic acid
Mannosaccharic acid
Gulosaccharic acid
Idosaccharic acid
Galactosaccharic acid, and
Talosaccharic acid.

Examples where $X^1$ is a cation, are the monovalent alkali metal cations Na+ and K+.

Further examples where $X^1$ is a cation are substituted ammonium cations, such as diethanolammonium and triethanolammonium cations.

Examples where $X^2$ is an alkyl group are methyl, ethyl, n-propyl, n-butyl, n-octyl and lauryl.

Examples where $Y^1$, $Y^2$, $Y^3$ and $Y^4$ are alkyl groups, are methyl and ethyl.

Examples where $Y^1$, $Y^2$, $Y^3$ and $Y^4$ are acyl group, are acetyl and propionyl.

A particularly preferred hexosaccharic acid is glucosaccharic acid (also known as saccharic acid or glucaric acid, and hereinafter referred to as glucaric acid) having the structure (2):

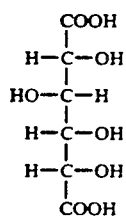

A particularly stable salt of glucaric acid which is preferred, is the disodium salt.

It is to be understood that in addition to an hexosaccharic acid, there will also be present in the composition other materials derived from this acid. In the case, for example of glucaric acid, the corresponding -1,4 lactone, -6,3-lactone and -1,4:6,3-dilactone and other minor species may also be present, their respective amounts depending on factors such as pH, temperature and the choice of vehicle. These other materials may also have a positive benefit on hair growth, either in their own right, or following conversion to glucaric acid, as could occur at or near neutral pH.

The total amount of hexosaccharic acid, or salt or ester thereof, as the hair growth promoter, present in the composition according to the invention is sufficient to increase hair growth in the rat, the model selected for this test, when said composition is applied topically thereto by, over a period of no more than 3 months, at least 10% more than that obtainable using a control composition from which the promoter has been omitted, in accordance with the Rat Hair Growth Test to be described later.

Preferably, the amount the hair growth promoter should be sufficient to increase hair growth in the rat by at least 20%, more preferably by at least 30%, most preferably by at least 40% and ideally by at least 50%.

The sufficient amount of the promoter is from 0.0001 to 99%, preferably from 0.1 to 20% by weight of the composition.

Preservation of the Composition

The composition according to the invention is preserved in such a manner that it will enjoy an extended shelf life following manufacture and prior to sale and use. Ideally the composition will have an indefinite shelf life.

It is accordingly apparent that the hair growth promoter is particularly prone to attack by bacteria, moulds and fungi and other microbial influences, particularly at pH values near neutrality that characterise the preferred composition. The shelf-life of the composition can therefore be unacceptably short due to the biodegradation of the promoter, unless steps are taken to preserve the composition.

In order to be preserved, the composition will accordingly be free, or substantially free, from viable microbial contaminants that are capable of resulting in microbial spoilage of the composition, and/or biodegradation of the promoter prior to topical application of the composition to mammalian skin or hair. It is to be understood, however, that the invention is also concerned with compositions, as herein defined, which may contain viable but dormant micro organisms, such as bacterial spores, provided that the conditions of preservation do not result in substantial proliferation of the microorganisms prior to use of the composition.

Examples of methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Extremes of pH Value

The composition according to the invention can alternatively be preserved by adjusting its pH to values that are either too low (e.g. pH <2) or too high (e.g. pH >12) to permit significant proliferation of microbial contaminants. The pH of the composition can accordingly be adjusted to desired high or low values by addition of an alkali or acid as a pH adjustant.

(iii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 25%, the amount chosen being sufficient to arrest microbial proliferation.

(iv) Water Activity Depressants

The compositions according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, moulds and fungi will not proliferate.

OTHER INGREDIENTS

Vehicle

The composition according to the invention also optionally comprises a solid, semi-solid or liquid cosmetically and/or physiologically acceptable vehicle, to enable the promoter to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the inhibitor which therefore ensure that it can be applied to and distributed evenly over the hair and/or scalp at an appropriate concentration. The vehicle is preferably one which can aid penetration of the promoter into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders, some of which can also be employed to preserve the composition.

Examples of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of the promoter to the skin in an amount which is sufficient effectively to enhance hair growth. The amount of the vehicle can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer.

The activity enhancer can be chosen from a wide variety of molecules which can function in different ways to enhance the effects of the hair growth promoter. Particular classes of activity enhancers include other hair growth stimulants, penetration enhancers, cationic polymers and liposomes, whose presence can further improve the delivery of the promoter through the stratum corneum to its site of action in the immediate environment of the hair follicle.

Some activity enhancers can also function as vehicles for the hair growth promoter.

(a) Other Hair Growth Stimulants i. Examples of other substances which themselves possess the ability to stimulate or increase hair growth include;

Benzalkonium chloride
Benzethonium chloride
Phenol
Estradiol
Diphenhydramine hydrochloride
Chlorpheniramine maleate
Chlorophyllin derivatives
Cholesterol
Salicylic acid
Methionine
Cystine
Red pepper tincture
Benzyl nicotinate
dl-Menthol
Peppermint oil
Calcium pantothenate
Panthenol
Castor oil
Hinokitiol
Prednisolone
Resorcinol ii. Further substances which themselves possess the ability to increase the rate of terminal hair growth include:

α-1,4 esterified disaccharides described by Choay S.A. in EP-A-0 064 112, having the structure (3):

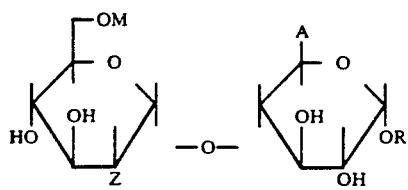

where
- Z represents a functional nitrogen group, such as an azide or a group having the structure —NHB, in which B represents —H or a functional group such as acetyl or sulphate as a salt with an organic or mineral cation;
- M represents —H or $SO_3M_1$, where $M_1$ is an organic or metallic cation, particularly an alkali metal; or an acetyl group;
- R represents a $C_1$ to $C_4$ alkyl radical, especially methyl; or an aryl radical;
- A represents a functional group such as an acid or —$COOR_1$, where $R_1$ represents —H or a $C_1$ to $C_4$ alkyl radical, especially methyl; or a metal, especially an alkali metal;

esterified oligosaccharides as described by Unilever in EP-A-0 211 610, including at least one esterified disaccharide unit consisting of a uronic acid residue having the structure (4a):

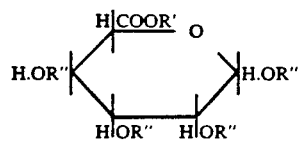

and a hexosamine residue having the structure: (5)

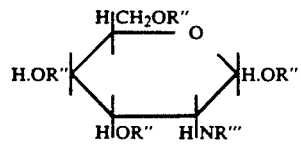

where
R' is —H, $C_3$ to $C_{10}$ alkyl or

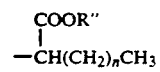

R" is —H, $C_1$ to $C_4$ alkyl, —$CO(CH_2)_mCH_3$, —$SO_3M$,

R'" is —H, —$CO(CH_2)_mCH_3$, or —$SO_3M$,

M is —H, or a metallic or organic cation n is 0 or an integer of from 1 to 7, and m is 0 or the integer 1 or 2;

the groups designated R" being the same or different, one R" group from each pyranose ring structure being linked by a glycosidic linkage having the configuration α-1,3, α-1,4, β-1,3 or β-1,4; and the —COR', —CH$_2$OR"

and —OR" groups being of either configuration with respect to the pyranose rings;

iii. Minoxidil and certain derivatives thereof as described by the Upjohn Co. in U.S. Pat. No. 3,461,461, iv. Minoxidil glucuronides, as described by Unilever in EP-0 242 967, v. Minoxidil sulphates, as described by The Upjohn Co. in WO 86/04231, vi. Ethylenediaminetetraacetic acid or salts thereof, as described by Redken Laboratories, Inc. in U.S. Pat. No. 4,814,351.

vii. Aldonolactones, such as D-glucaro-1,4-lactone, as described by Unilever in EP-0 277 428.

viii. Direct proteoglycanase inhibitors, such as 1,10-phenanthroline, as described by Unilever in EP-0 277 428.

ix. Glycosaminoglycanase inhibitors, as described by Unilever in EP-0 277 428, such as aldonolactones and esterified aldonolactones having the structure (5):

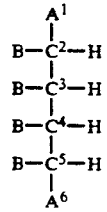

where
A¹ and A² are —H,

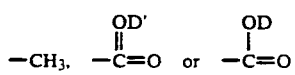

B is OD″ or a lactone linkage to position 1 or 6, or —NHCOCH₃
and where D is —H or $C_2$ to $C_8$ alkyl,
D′ is the remainder of the molecule joined through another C atom at positions 2 to 5 to form a lactone,
D″ is —H or $C_2$ (ie acetyl) to $C_4$ acyl of either configuration with respect to the backbone of this molecule;
preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone.

x. Glycosaminoglycanase inhibitors, as described by Unilever in EP 0 277 428, such as monosaccharides and esterified monosaccharides having the structure (6):

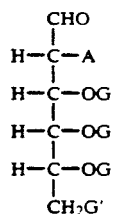

where
A is —OG or —NHCOCH₃
G is —H, —SO₃M″, $C_2$ (ie acetyl) to $C_4$ acyl
G′ is —H or —OG
M″ is —H or a metal cation
wherein the functional groups can be in either configuration with respect to the backbone of the above molecule;
preferred examples of which include:
N-Acetylglucosamine
N-Acetylgalactosamine
D-Galactosamine
D-Glucosamine-3-sulphate
N-Acetylmannosamine.

xi. Glycosaminoglycan chain cellular uptake inhibitors, as described by Unilever in EP 0 277 428, such as hexuronic acid and esters thereof which may be represented by the generic structure (7):

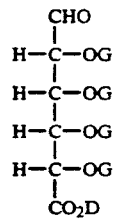

where
G is —H, —SO₃M″, $C_2$ (ie acetyl) to $C_4$ acyl;
D is —H or $C_2$ to $C_8$ alkyl
M″ is —H or a metal cation;
wherein the functional groups can be in either configuration with respect to the backbone of the above molecule;

xii. Chemical inhibitors of glycosidase activity, as described by Unilever in EP 0 334 586, chosen from lactams having the structure (8):

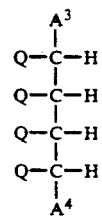

where A³ and A⁴ are —H, —CH₃,

—CH₂OT or

A³ and A⁴ being the same or different, and at least one of which being the group:

in a lactam ring;
and where Q is —OT′, —NHT′ or a lactam linkage to A³ or A⁴;
the Q groups being the same or different, and at least one of which is involved in a lactam linkage;
and where T is the same or different and is chosen from
—H, —$C_pH_{2p+1}$ or a metal ion,
T′ is —H or —$COC_pH_{2p+1}$, and
p is an integer of from 1 to 22;
provided that:
where any of the Q groups is
—OT′ or —NHT′,
then that group or groups can be of either stereochemical configuration with respect to the plane of the ring,
preferred examples of which include:
D-glucaro-1,5-lactam L-Galactono-1,4-lactam, L-Arabino-1,5-lactam, D-Fucono-1,5-lactam,
D-Glucaro-1,4-lactam, D-Glucurono-6,3-lactam,
1,2,5-tri-0-acetyl-D-glucurono-6,3-lactam
2-Acetamido-2-deoxygluconolactam,
2-Acetamido-2-deoxygalactonolactam,
D-Glucaro-1,4:6,3-dilactam, L-Idaro-1,4-lactam,
2,3,5-Tri-0-acetyl-D-glucaro-1,4-lactam,
2,5-Di-0-acetyl-D-Glucaro-1,4:6,3-dilactam,
D-glucaro-1,5-lactam ethyl ester;

xiii. Chemical activators of protein kinase C enzymes, as described by Unilever in EP 0 334 585 chosen from diacylglycerols having the structure (9):

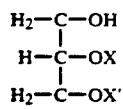
(9)

where X and X' are the same or different and is represented by the grouping:

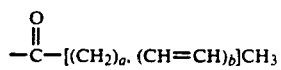

where x is 0 or an integer of from 1 to 28, and y is 0 or an integer of from 1 to 5;

the X and X' groups being of either stereochemical configuration with respect to the carbon backbone of the glycerol molecule;
preferred examples of which include:
1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeoicosanoyl-sn-glycerol.

xiv. Glycosaminoglycanese inhibitors, as described by Unilever in EPA 89306278.6, chosen from aldonomonolactone or alduronomonolactone derivatives having the structure (10):

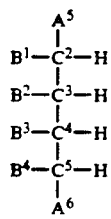
(10)

where $A^5$ is

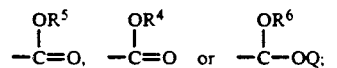

$A^6$ is 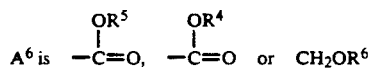

$B^1$, $B^2$, $B^3$ and $B^4$ are each chosen from is $OR^5$, $NHR^6$, $NHR^7$ or a lactone linkage to position 1 or 6, and/or an ether linkage to $Q^1$;

said substituents B being the same or different, and being in either configuration, with respect to the backbone of the above structure, on positions $C^2$ to $C^5$ not involved in a lactone ring;
and where $R^4$ is —H, $C_1$ to $C_{20}$ alkyl, a metal cation, $NH_4+$ or an alkanolamine cation;
$R^5$ is the remainder of the molecule joined through another C atom at positions 2 to 5 to form a lactone;
$R^6$ is —H, —$CH_3$, benzyl or $C_2$ to $C_6$ acyl;
$R^7$ is —H, —$CH_3$, benzyl or $C_3$ to $C_6$ acyl;
$Q^1$ is the remainder of the molecule joined through an ether linkage to either $C^4$ or $C^5$, forming either a pyranose or furanose ring;
provided that, when $A^5$ is

then $A^6$ is

provided also that, when $A^6$ is $CH_2OH$, then one or more of the B substituents is —$CH_3$, $C_2$ to $C_4$ acyl or $NHR^7$;
provided also that, when $A^5$ is

and all $B^1$, $B^2$, $B^3$ and $B^4$ substituents are —OH, then $A^6$ is

or $CH_2OR^6$, and $R^4$ is $C_1$ or $C_9$ to $C_{20}$ alkyl;

preferred examples of which aldonomonolactone derivatives include:
6-acetyl-galactono-1,4-lactone
6-propionyl-galactono-1,4-lactone
6-butyryl-galactono-1,4-lactone
2-propionamido-2-deoxygluconolactone
2-butyramido-2-deoxygluconolactone
2-propionamido-2-deoxygalactonolactone
2-butyramido-2-deoxygalactonolactone
6-propionyl-2-acetamido-2-deoxygluconolactone diacetyl-6-propionyl-2-acetamido-2-deoxygluconolactone
6-butyryl-2-acetamido-2-deoxygalactonolactone diacetyl-6-butyryl-2-acetamido-2-deoxygalactonolactone 2,3,5,6-tetraacetyl-galactono-1,4-lactone
2,3,5-triacetyl-6-propionylgalactono-1,4-lactone
triacetyl-2-propionamido-2-deoxygalactonolactone
triacetyl-2-butyramido-2-deoxygluconolactone
6-methyl-glucaro-1,4-lactone
2,3,5,6-tetramethyl-glucaro-1,4-lactone
6-methyl-2,3,5-triacetylglucaro-1,4-lactone
6-methyl-3-methyl-glucaro-1,4-lactone, and
6-methyl-3-acetyl-glucaro-1,4-lactone;

and a preferred example of which alduronomonolactone derivative is:

1,2,5-triacetyl-glucurono-6,3-lactone.

xv. Glycosaminoglycanase inhibitors, as described by Unilever in EPA 89306278.6, chosen from acylated monosaccharides having the structure (11):

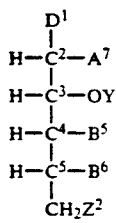
(11)

where $A^7$ is —OY or —NHR$^8$ $B^5$ and $B^6$ are each chosen from is —OY, or an ether linkage to $D^1$, $D^1$ is

where $X^2$ is an ether linkage either to $C^4$ or $C^5$ forming a pyranose or furanose ring;

Y is —H, —SO$_3$M, C$_2$ to C$_4$ acyl or C$_1$ to C$_{18}$ alkyl;

said substituents $A^7$, $B^5$, $B^6$ and —OY being the same or different, and being in either configuration, with respect to backbone of the above structure;

and where $Z^1$ is —H or —OY $R^8$ is —H, —SO$_3$M$^2$ or C$_3$ or C$_4$ acyl, $M^2$ is —H, a metal cation, NH$_4$+, or an alkanolamine cation;

provided that, when $R^8$ is —H, then 1 or more of Y is chosen from —SO$_3$M$^2$ or C$_2$ to C$_4$ acyl; and mixtures thereof.

Preferred examples of which acylated monosaccharides include:
2-propionamido-2-deoxyglucose
1,3,4,6-tetraacetyl-2-propionamido-2-deoxyglucose
2-butyramido-2-deoxygalactose
1,3,4,6-tetraacetyl-2-butyramido-2-deoxygalactose
2-sulphamido-2-deoxygalactose
2-sulphamido-2-deoxyglucose
2-butyramido-2-deoxymannose
1,3,4,6-tetraacetyl-2-butyramido-2-deoxyglucose
2-butyramido-2-deoxyglucose, and
1,3,4,6-tetraacetyl-2-butyramido-2-deoxyglucose.

xvi. Esters of pyroglutamic acid, as described by Lever Brothers Company in U.S. Pat. No. 4,774,255, having the structure (12):

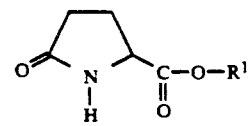
(12)

where $R^1$ is C$_1$ to C$_{30}$ aklyl

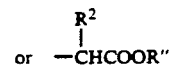

and where $R^2$ and $R^3$ are the same or different and are each represented by H or the grouping (13):

[(CH$_3$)$_u$, (CH$_2$OH)$_v$, (CH$_2$)$_w$, (CH$_3$CH$_2$)$_x$,    (13)

(CHOH)$_y$, (CH=CH)$_z$]— where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 4, and
u+v+w+x+y+z is an integer of from 1 to 22;
provided that when the subgrouping (CH=CH) is present, then the total number of carbon atoms in said grouping is from 10 to 22.

Examples of suitable esters of pyroglutamic acid where $R^1$ in structure (12) is C$_1$ to C$_{30}$ alkyl are:
pyroglutamic acid methyl ester
pyroglutamic acid ethyl ester
pyroglutamic acid n-propyl ester
pyroglutamic acid n-butyl ester
pyroglutamic acid n-hexyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where $R^1$ in structure (12) is C$_1$ to C$_{14}$ alkyl, (linear or branched), especially C$_1$ to C$_6$ (linear or branched).

Further examples of preferred esters of pyroglutamic acid, where $R^1$ in structure (12) is

are those where $R^2$ and/or $R^3$ having the structure shown for grouping (13), include straight and branched chain, saturated or unsaturated aliphatic groups having from 1 to 22 carbon atoms, such as the alkyl groups:

methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl.

and the $C_{10-22}$ alkenyl groups:
linoleyl
linolenyl
α-linolenyl
arachidonyl, and
columbinyl.

Further examples of the grouping (13) also include hydroxyalkyl groups having from 1 to 22 carbon atoms, such as:

hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

Further specific examples of esters of pyroglutamic acid which are particularly suited for use as other hair growth stimulants are:

2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

(b) Penetration Enhancers

As has been stated earlier, the presence of a penetration enhancer can potentiate the benefit of the hair growth promoter, by improving its delivery through the stratum corneum to its site of action in the immediate environment of the hair follicle close to the dermal papilla.

The penetration enhancer can accordingly function in a variety of ways. It can for example, improve the distribution of the hair growth promoter on the skin surface or, it can increase its partition into the skin from the composition when applied topically, so aiding its passage to its site of action. Other mechanisms enhancing the benefit of the promoter may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid,
Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include surface active agents, preferred examples of which include:

(i) Anionic surface active agents, such as metallic or alkanolamine salts of fatty acids for example sodium laurate and triethanolamine oleate;
  alkyl benzene sulphonates, for example triethanolamine dodecyl benzene sulphonate;
  alkyl sulphates, for example sodium lauryl sulphate;
  alkyl ether sulphates, for example sodium lauryl ether sulphate [2 to 8 EO];
  sulphosuccinates, for example sodium dioctyl sulphonsuccinate;
  monoglyceride sulphates, for example sodium glyceryl monostearate monosulphate;
  isethionates, for example sodium isethionate;
  methyl taurides, for example Igepon T;
  acylsarcosinates, for example sodium myristyl sarcosinate;
  acyl peptides, for example Maypons and Lamepons;
  acyl lactylates,
  polyalkoxylated ether glycollates, for example trideceth-7 carboxylic acid;
  phosphates, for example sodium dilauryl phosphate.

(ii) Cationic surface active agents, such as amine salts, for example sapamin hydrochloride;
  quartenary ammonium salts, for example Quaternium 5, Quaternium 31 and Quaternium 18;

(iii) Amphoteric suface active agents, such as imidazol compounds, for example Miranol;
  N-alkyl amino acids, such as sodium cocaminopropionate and asparagine derivatives;
  betaines, for example cocoamidopropylbetaine (iv) Nonionic surface active agents, such as fatty acid alkanolamides, for example oleic ethanolamide;
  esters of polyalcohols, for example Span;
  polyglycerol esters, for example that esterified with $C_{12-18}$ fatty acids and one or several OH groups;
  polyalkoxylated derivatives. for example polyoxy-polyoxyethylene stearate, and octylphenoxy polyethoxyethanol (TRITON X-100 available from Rohm & Haas, or e.g. CIRRASOL available from I.C.I.)
  ethers, for example polyoxyethylene lauryl ether;
  ester ethers, for example Tween;
  amine oxides, for example coconut and dodecyl dimethyl amine oxides.

Mixtures of two or more of the above surface active agents can be employed in the composition according to the invention.

(c) cationic polymer chosen from;
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride)
Poly(diallylpiperidinium chloride)
Poly(vinyl pyridinium chloride)
Quarternised poly (vinyl alcohol)
Quarternised poly (dimethylaminoethylmethacrylate); and
mixtures thereof The amount of activity enhancer, when employed in accordance with the invention, will normally be from 0.1 to 50%, preferably from 0.5 to 25% and most preferably from 0.5 to 10% by weight of the composition.

Other Hair Growth Promoter Adjuncts

There is evidence of an inflammatory component in the development of male pattern baldness and for this reason it is advantageous to include in the compositions according to the invention agents which will suppress the inflammatory process. Such agents, which include steroidal and non-steroidal anti-inflammatory compounds (e.g. hydrocortisone and ibuprofen respectively), further enhance the hair growth promoting benefits of the hexasaccharic acid and their derivatives as herein defined, and compositions containing them, in accordance with the invention.

The composition according to the invention can also contain adjuncts other than those already mentioned, depending on the form of the intended product. It is, for example, possible to include antiseptics, antioxidants, emulsifiers, sequestrants, such as ethylene diamine, tetracetic acid and colouring agents, which can improve the stability and consumer appeal of the composition.

The composition according to the invention can also be employed as a vehicle for a wide variety of cosmetically or pharmaceutically active ingredients, particularly ingredients which have some beneficial effect other than the promotion of hair growth when applied to the skin.

Process

The invention also provides a process for the preparation of a composition suitable for promoting hair growth which comprises mixing a hexosaccharic acid, or a salt or ester thereof, as a hair growth promoter, with a chemical preservative, or preserving it by other means, as herein before defined, to provide a composition according to the invention, in which the promoter forms from 0.0001 to 99% by weight of the composition.

Product Form and Container

The compositions of the invention can be formulated as liquids, for example as a lotion, shampoo, milk, cream or mousse for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Hair Growth Promoter for Inducing, Maintaining or Increasing Hair Growth The invention also provides for the use of the promoter, as herein defined, and compositions containing it for topical application to mammalian skin or hair for inducing, maintaining or increasing hair growth.

The compositions according to the invention are primarily intended for topical application to the scalp of the human subject, particularly where the head is already bald or balding, in order to promote the regrowth of terminal hair. The compositions can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5 g daily containing from 0.00001 to 1 g of a selected hair growth promoter over the period of at least six months will in most cases result in an improvement in hair growth.

EVALUATION OF EFFICACY OF HAIR GROWTH PROMOTERS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat housed individually to prevent licking.

In each comparison, 10 rats were used in each group and hair growth was assessed as follows:

A small patch of normal skin (4 cm×4 cm) on the upper back of each rat was clipped at the start and 0.3 ml of a hair growth stimulant composition (or a control) applied topically twice daily and once on Saturdays and Sundays to each clipped area. The concentration of test compound in the composition was chosen from 0.01 to 20% w/v.

It is to be understood that the potency of each hair growth promoter in terms of its ability to induce, maintain or increase hair growth is unlikely to be uniform, some being more potent than others, and therefore the concentration of any promotor chosen for thorough evaluation must be carefully selected after preliminary testing to determine its potential as a hair growth promoter. In any case, this concentration will lie within the range of from 0.01 to 20% w/v as stipulated above.

Hair was clipped from the area of the patch twice weekly, collected and weighed at each time point over a standard period of 3 months, and cumulative hair weight calculated. From these data, it was possible to estimate the effect of a promoter as a hair growth stimulant (test compound) on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the hair growth promoter is assessed compound by the Rat Hair Growth Test, an increase of at least 10% by weight of hair after 3 months treatement will be obtained. Usually, the 10% by weight minimum value will be attained well before the end of this 3 months period.

Validation of Rat Model for Hair Growth Using Minoxidil

The rat model was validated by showing that twice daily topical application of a known promoter of human hair growth, namely 2% (w/v) minoxidil in a vehicle of 70% ethanol, 20% water and 10% propylene glycol, caused a significant increase of 25% in hair growth as shown below:

TABLE 1

| Treatment | Mean Cumulative Hair weight (mg) ± sd, after 52 days | Significance Level (vs vehicle) |
|---|---|---|
| 2% minoxidil | 786.2 ± 94.8 | p = 0.002* |
| Vehicle (control) | 628.3 ± 90.0 | |

*statistically significant

Measurement of Hair Growth Following Topical Application of the Disodium Salt of Glucaric Acid Topical treatment with a composition according to the invention was found to stimulate hair growth. In this example, the effect of topical application of the disodium salt of glucaric acid is shown. The test solution in this experiment contained 10, 15 or 20% (w/v) of the glucaric acid disodium salt in the form of a solution in a vehicle composed of 20% (v/v) ethanol, 0.1% (w/v) TRITON x-100 and 1% (w/v) citric acid adjusted to pH7 with sodium hydroxide. The control solution contained no glucaric acid disodium salt. Test or control solutions (0.3 ml) were applied topcally twice daily and once on Saturdays and Sundays to the clipped area. The hair growth results are shown in Table 2.

TABLE 2

| Treatment | Mean Cumulative Hair weight (mg) ± sd, after 57 days | Significance Level (vs vehicle) |
|---|---|---|
| 10% Glucaric acid | 589 ± 90.64 | NS |
| Vehicle (Control) | 563.10 ± 81.52 | (P = 0.5) |
| 15% Glucaric acid | 646 ± 101.79 | S |
| Vehicle (Control) | 517.50 ± 66.36 | (P = 0.004) |
| 20% Glucaric acid | 998.27 ± 142.83 | S |
| Vehicle (Control) | 763.75 ± 138.24 | (P = 0.002) |

S statistically significant
NS not statistically significant

In addition to demonstrating a statistically significant stimulation of hair growth (up to 30% increase) as shown in Table 2, the glucaric acid disodium salt has consistently been found to advance anagen, thus reducing the amount of time spent in the resting stage of hair cycle.

EXAMPLES

The invention is illustrated by the following examples, each of which includes a hair growth promoter. Each formulation is preserved, either by irradiation or by the addition of a chemical preservative.

Furthermore, each of the formulations which features in these examples of compositions according to the invention, is capable of increasing hair growth in the rat, when applied thereto, by at least 10% more than that obtainable using a control composition from which the hair growth promoter has been omitted. It will be appreciated, however, that for human use, those of the following formulations which are "rinse off" products such as hair shampoo, will generally require repeated application to the hair or scalp before significant hair growth is observed.

EXAMPLE 1

This Example illustrates a lotion according to the invention which is suitable for topical application to the scalp in order to promote hair growth.

The lotion has the following formulation:

|  | % w/v |
|---|---|
| Glucaric acid, methyl ester | 5 |
| ethanol | 45 |
| perfume | q.s. |
| water | to 100 |

EXAMPLE 2

This Example illustrates a hair tonic which is suitable for application to hair or scalp.

The hair tonic has the following formulation:

|  | % w/v |
|---|---|
| disodium glucarate | 15 |
| ethanol | 20 |
| perfume | q.s. |
| water | to 100 |

EXAMPLE 3

This Example also illustrates a lotion which is suitable for topical application to the scalp.

The lotion has the following formulation:

|  | % w/v |
|---|---|
| glucaric acid | 15 |
| propan-2-ol | 10 |
| ethanol | 20 |
| triethanolamine | q.s.* |
| perfume | to 100 |

*sufficient to adjust the pH to a value of from 4 to 8.

EXAMPLE 4

This Example also illustrates a hair tonic which is suitable for application to hair or scalp.

The hair tonic has the following formulation:

|  | % w/v |
|---|---|
| glucaric acid | 20 |
| ethanol | 40 |
| triethanolamine | q.s.* |

-continued

|  | % w/v |
|---|---|
| perfume | q.s. |
| water | to 100 |

*sufficient to adjust to pH to a value of from 4 to 8.

EXAMPLES 5 TO 8

The following formulations represent lotions which can be used topically in the treatment of bald or balding male or female heads.

|  | % w/v | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Sodium talosaccharate | 5 | — | — | — |
| Sodium glucarate | — | 1 | — | — |
| di-(diethanolamine) glucarate | — | — | 0.8 | — |
| di-(triethanolamine) glucarate | — | — | — | 0.6 |
| Perfume | 1 | 1 | 1 | 1 |
| Water | to 100 | 100 | 100 | 100 |

EXAMPLES 9 TO 12

The following formulations represent creams which can be used in the treatment of baldness.

|  | % w/v | | | |
|---|---|---|---|---|
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| Glucaric acid | 2 | — | — | — |
| Monomethyl gluconate | — | — | — | 1 |
| Diethyl glucarate | — | 1.5 | — | — |
| Monooctyl glucarate | — | — | 2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water | to 100 | 100 | 100 | 100 |

The following examples 13 to 17 illustrate shampoos for use in washing the hair and scalp, and for promoting hair growth on the scalp.

EXAMPLE 13

|  | % w/v |
|---|---|
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| Mannosaccharic acid, lactyl ester | 5 |
| Perfume | q.s. |

EXAMPLE 14

|  | % w/v |
|---|---|
| Sodium lauryl ether sulphate (2 EO) [100% AD] | 12 |
| POLYMER JR400 | 2.5 |
| BRIPHOS 03D | 2.5 |
| Galactosaccharic acid, ester | 4 |
| Perfume | q.s. |
| Water | to 100 |

EXAMPLE 15

|  | % w/v |
|---|---|
| Monoethanolamine lauryl sulphate [100% AD] | 20 |
| JAGUAR C13S | 3 |
| BRIPHOS 03D | 1.7 |
| Coconut diethanolamide | 5 |
| D-Glucaro-1,4-lactone | 1 |
| Sodium allosaccharate | 3 |
| Perfume | q.s. |
| Water | to 100 |
| pH adjusted to 6.5 |  |

EXAMPLE 16

|  | % w/v |
|---|---|
| Sodium lauryl ether sulphate (3 EO) [100% AD] | 12 |
| JAGUAR C13S | 0.3 |
| BRIPHOS 03D | 1 |
| N-Acetylglucosamine | 2 |
| Mono (triethanolamine) altrosaccharate | 4 |
| Perfume | q.s. |
| Water | to 100 |
| pH adjusted to 6.5 |  |

EXAMPLE 17

|  | % w/v |
|---|---|
| Sodium lauryl ether sulphate (2 EO) [100% AD] | 12 |
| POLYMER JR400 | 3 |
| BRIPHOS 03D | 1 |
| Opacifier | 9 |
| Monopotassium gulosaccharate | 5 |
| Perfume | q.s. |
| Water | to 100 |
| pH adjusted to 6.5 |  |

EXAMPLE 18

The following example illustrates a lotion according to the invention which can be applied topically to the scalp to prevent hair loss and stimulate hair regrowth.

|  | % w/v |
|---|---|
| Sodium idosaccharate | 7 |
| Minoxidil | 2 |
| ethanol | 16 |
| citric acid | 1.05 |
| water | to 100 |
| pH adjusted to 4.2 with sodium hydroxide |  |

EXAMPLE 19

This example illustrates a lotion for topical application to the skin in order particularly to demonstrate significant hair growth.

A concentrate was prepared by mixing together the following ingredients:

|  |  |
|---|---|
| Glucaric acid solution* | 30 ml |
| Ethanol | 20 ml |
| 10% w/w aqueous solution of TRITON-X100 | 1 ml |
| Citric acid | 1 g |
| Water | 20 ml |

The glucaric acid solution was a boiled equilibrium mixture containing 37% solids w/v, and had a pH value of 1.5. The composition of this solution, with respect to the solids was 30 parts by weight glucaro-1,4-lactone, 30 parts by weight glucaro-3,6-lactone and 40 parts by weight of glucaric acid.

The mixture was then titrated with 10N sodium hydroxide to a pH value of 4.2 to provide the concentrate.

The concentrate was finally diluted to 100 ml with water to provide the lotion.

Topical application to the rat model of the products described in Examples 1 to 19, over a period of no more than 3 months, will increase hair growth by an amount which is at least 10% more than that achievable following topical application of a similar product from which the hexosaccharic acid, esters or salts thereof have been omitted, in accordance with the Rat Hair Growth Test as described herein.

We claim:

1. A method for inducing, maintaining or increasing hair growth which comprises topically applying a preserved composition to mammalian skin and hair, in a mammal having need thereof, said composition comprising a hexosaccharic material selected from the group consisting of hexosaccharic acid, salts of hexosaccharic acid and esters of hexosaccharic acid, said hexosaccharic material being present in an effective amount to induce, maintain or increase hair growth, said hexosaccharic material having the structure (1):

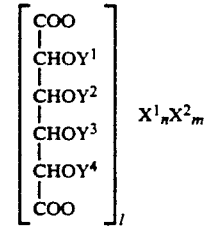

where
X$^1$ is chosen from H, alkali metal, ammonium and substituted ammonium counterions;
X$^2$ is chosen from an alkyl or hydroxyalkyl group having from 1 to 18 carbon atoms;
Y$^1$, Y$^2$, Y$^3$ and Y$^4$ are each chosen from H, and alkyl group having from 1 to 12 carbon atoms, and an acyl group having from 1 to 18 carbon atoms;
l is an integer from 1 to 3;

m and n are each 0 or the integer 1 or 2; and m+n is 1 or 2; and a cosmetically acceptable vehicle.

2. The method of claim 1, wherein the hexosaccharic acid is selected from the group consisting of:

Allosaccharic acid

Altrosaccharic acid

Glucosaccharic acid

Mannosaccharic acid

Gulosaccharic acid

Galactosaccharic acid, and

Talosaccharic acid.

3. The method of claim 1, wherein the salt of the hexosaccharic acid is a monovalent alkali metal salt, the counterion being selected from the group consisting of sodium and potassium.

4. The method of claim 3, wherein the salt of the hexosaccharic acid is the disodium salt of glucosaccharic acid.

5. The method of claim 1, wherein the salt of the hexosaccharic acid is a substituted ammonium salt, the counterion being selected from the group consisting of diethanolammonium and triethanolammonium.

6. The method of claim 1, wherein the ester of the hexosaccharic acid is selected from the group consisting of alkyl and hydroxyalkyl esters in which the ester group has from 1 to 18 carbon atoms.

7. The method of claim 1, , wherein the effective amount of the hair growth promoter present in the composition is from 0.0001 to 99% by weight.

8. The method of claim 1, wherein said cosmetically acceptable vehicle is present from 1 to 99.99% by weight.

9. The method of claim 1 further comprising minoxidil.

10. A method for converting vellus hair to growth as terminal hair which comprises the step of applying to the scalp in the region of vellus hair an effective amount of the composition in accordance with claim 1.

11. A method for increasing the rate of terminal hair growth, which comprises the step of applying to the scalp in the region of terminal hair an effective amount of the composition in accordance with claim 1.

* * * * *